United States Patent [19]

Berg et al.

[11] Patent Number: 4,544,454

[45] Date of Patent: * Oct. 1, 1985

[54] SEPARATION OF ISOPROPYL ETHER FROM METHYL ETHYL KETONE BY EXTRACTIVE DISTILLATION

[76] Inventors: Lloyd Berg, 1314 S. Third Ave.; An-I Yeh, 709 S. 12th Ave., both of Bozeman, Mont. 59715

[*] Notice: The portion of the term of this patent subsequent to Jul. 10, 2001 has been disclaimed.

[21] Appl. No.: 578,869

[22] Filed: Feb. 10, 1984

Related U.S. Application Data

[62] Division of Ser. No. 488,398, Apr. 25, 1983, Pat. No. 4,459,178.

[51] Int. Cl.$^4$ .............................................. B01D 3/40
[52] U.S. Cl. ........................................ 203/51; 203/56; 203/57; 203/58; 203/60; 203/64; 568/410; 568/699
[58] Field of Search ....................... 568/699, 410, 411; 203/51, 56, 57, 58, 60, 64

[56] References Cited

U.S. PATENT DOCUMENTS

| | | | |
|---|---|---|---|
| 2,623,845 | 12/1952 | Coutor | 203/51 |
| 3,198,837 | 8/1965 | Smidt et al. | 568/410 |
| 3,228,985 | 1/1966 | Carpenter et al. | 568/410 |
| 3,709,928 | 1/1973 | Murayama et al. | 203/64 |
| 4,459,179 | 7/1984 | Berg et al. | 203/60 |
| 4,469,491 | 9/1984 | Finkel | 203/42 |
| 4,470,881 | 9/1984 | Berg | 203/51 |

FOREIGN PATENT DOCUMENTS

| | | | |
|---|---|---|---|
| 234662 | 12/1963 | Austria | 203/58 |
| 967471 | 12/1960 | United Kingdom | 203/60 |

*Primary Examiner*—Wilbur Bascomb

[57] ABSTRACT

Isopropyl ether cannot be completely removed from isopropyl ether - methyl ethyl ketone mixtures by distillation because of the presence of the minimum binary azeotrope. Isopropyl ether can be readily removed from mixtures containing it and methyl ethyl ketone by using extractive distillation in which the extractive distillation agent is a higher boiling oxygenated and/or nitrogenous organic compound or a mixture of these. Typical examples of effective agents are adiponitrile; ehtylene carbonate plus dimethylformamide; adiponitrile plus dimethylformamide plus glycerine.

8 Claims, No Drawings

SEPARATION OF ISOPROPYL ETHER FROM METHYL ETHYL KETONE BY EXTRACTIVE DISTILLATION

This application is a divisional of U.S. Pat. No. 4,459,178 issued July 10, 1984 which was application Ser. No. 488,398 filed Apr. 25, 1983.

FIELD OF THE INVENTION

This invention relates to a method for separating isopropyl ether from methyl ethyl ketone using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus requires either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Two of the most commonly used solvents in the chemical industry are isopropyl ether and methyl ethyl ketone. Normally mixtures of solvents are recovered by fractionation in a multiplate rectification column and the ease of separation depends upon the difference in boiling points of the compounds to be separated. However isopropyl ether, b.p.=68.3° C. and methyl ethyl ketone, b.p.=79.6° C. form a minimum azeotrope boiling at 65° C. at one Atm. pressure and containing 87.6 wt.% isopropyl ether, 12.4 wt.% methyl ethyl ketone. It is therefore impossible to produce pure isopropyl ether from isopropyl ether—methyl ethyl ketone mixtures by rectification because the lower boiling azeotrope will always come off overhead as the initial product. Any mixture of isopropyl ether and methyl ethyl ketone subjected to rectification at one atmosphere pressure will produce an overhead product boiling at 65° C. and containing 87.6 wt.% isopropyl ether, 12.4 wt.% methyl ethyl ketone. Extractive distillation would be an attractive method of effecting the separation of isopropyl ether from methyl ethyl ketone if agents can be found that (1) will break the isopropyl ether—methyl ethyl ketone azeotrope and (2) are easy to recover from the methyl ethyl ketone, that is, form no azeotrope with methyl ethyl ketone and boil sufficiently above methyl ethyl ketone to make the separation by rectification possible with only a few theoretical plates.

Extractive distillation typically requires the addition of an equal amount to twice as much extractive agent as the isopropyl ether—methyl ethyl ketone on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with methyl ethyl ketone otherwise it will form a two phase azeotrope with the methyl ethyl ketone in the recovery column and some other method of separation will have to be employed.

The breaking of an azeotrope by extractive distillation is a new concept. One application of this concept might be the breaking of the ethanol-water azeotrope. J. Schneible, (U.S. Pat. No. 1,469,447) used glycerol; P. V. Smith & C. S. Carlson (U.S. Pat. No. 2,559,519) employed ethoxyethanol and butoxyethanol for this purpose and W. E. Catterall, (U.S. Pat. No. 2,591,672) reported gasoline as being effective. These are dehydrations and operate more conventionally as a solvent extraction process rather than an extractive distillation. The closest process to this system is probably the breaking of the ethyl acetate—ethanol-water azeotrope by extractive distillation reported by Berg and Ratanapupech (U.S. Pat. No. 4,379,028, Apr. 5, 1983).

OBJECTIVE OF THE INVENTION

The object of this invention is to provide a process or method of extractive distillation that will enhance the relative volatility of isopropyl ether from methyl ethyl ketone in their separation in a rectification column. It is further object of this invention to identify suitable extractive distillation agents which will eliminate the isopropyl ether—methyl ethyl ketone azeotrope and make possible the production of pure isopropyl ether and methyl ethyl ketone by rectification. It is a further object of this invention to identify organic compounds which, in addition to the above constraints, are stable, can be separated from methyl ethyl ketone by rectification with relatively few plates and can be recycled to the extractive distillation column and reused with little decomposition.

SUMMARY OF THE INVENTION

The objects of this invention are provided by a process for separating isopropyl ether from methyl ethyl ketone which entails the use of certain oxygenated, nitrogenous and/or sulfur containing organic compounds as the agent in extractive distillation.

DETAILED DESCRIPTION OF THE INVENTION

We have discovered that certain oxygenated, nitrogenous and/or sulfur containing organic compounds, some individually but principally as mixtures, will effectively negate the isopropyl ether—methyl ethyl ketone azeotrope and permit the separation of pure isopropyl ether from methyl ethyl ketone by rectification when employed as the agent in extractive distillation. Table I lists the compounds, mixtures and approximate proportions that we have found to be exceptionally effective. Table II lists the compounds, mixtures and approximate proportions that are successful but do not give quite as high a relative volatility as that obtained from those in Table I. Table III lists those mixtures which we found to be relatively unsuccessful. The data in Table I, II and III were obtained in a vapor-liquid equilibrium still. In each case, the starting material was a 50–50 wt.% mixture of isopropyl ether and methyl ethyl ketone. The ratios are the parts by weight of extractive agent used per part of isopropyl ether—methyl ethyl ketone mixture. The relative volatilities are listed for each the two ratios employed.

The compounds that are effective as extractive distillation agents when used alone are ethylene carbonate, propylene carbonate, adiponitrile, dimethylformamide, sulfolane and nitrobenzene. The compounds that are effective when used in mixtures of two or more components are ethylene glycol, propylene glycol, 1,4-butanediol, 1,5-pentanediol, neopentyl glycol, 1,6-hexanediol, hexylene glycol, diethylene glycol, triethylene glycol, tetraethylene glycol, dipropylene glycol, glycerine, 3-chloro-1,2-propanediol, dimethylsulfoxide, dimethylformamide, sulfolane, ethylene carbonate, propylene carbonate, adiponitrile, nitrobenzene, methyl isoamyl ketone, hexyl acetate and propoxypropanol.

TABLE 1

Extractive Distillation Agents Which Are Exceptionally Effective In Separating Isopropyl Ether From Methyl Ethyl Ketone.

| Compounds | Ratios | | Relative Volatilities | |
|---|---|---|---|---|
| Ethylene carbonate | 1 | 6/5 | 8.91 | 8.35 |
| Adiponitrile, 1,4-Butanediol | $(1/2)^2$ | $(3/5)^2$ | 6.59 | 6.31 |
| Adiponitrile, Diethylene glycol | " | " | 5.94 | 6.58 |
| Adiponitrile, Triethylene glycol | " | " | 5.81 | 6.72 |
| Adiponitrile, Ethylene carbonate | " | " | 10.36 | 8.11 |
| Adiponitrile, Dimethylsulfoxide (DMSO) | " | " | 6.06 | 6.26 |
| Ethylene carbonate, Dimethylformamide (DMFA) | " | " | 6.58 | 7.07 |
| Ethylene carbonate, DMSO | " | " | 6.94 | 5.40 |
| Ethylene carbonate, Sulfolane | " | " | 6.80 | 6.81 |
| Sulfolane, DMSO | " | " | 6.05 | 6.54 |
| Sulfolane, Ethylene glycol | " | " | 5.70 | 6.50 |
| Adiponitrile, DMSO, Ethylene glycol | $(1/3)^3$ | $(2/5)^3$ | 6.68 | 7.02 |
| Adiponitrile, DMSO, Propylene glycol | " | " | 7.16 | 6.21 |
| Adiponitrile, DMSO, 1,4-Butanediol | " | " | 6.46 | 6.37 |
| Adiponitrile, DMSO, 1,5-Pentanediol | " | " | 5.93 | 6.08 |
| Adiponitrile, DMSO, Diethylene glycol | " | " | 6.40 | 5.83 |
| Adiponitrile, DMSO, Triethylene glycol | " | " | 6.22 | 6.16 |
| Adiponitrile, DMSO, Tetraethylene glycol | " | " | 6.93 | 5.57 |
| Adiponitrile, DMSO, Glycerine | " | " | 8.21 | 8.12 |
| Adiponitrile, DMSO, Sulfolane | " | " | 6.20 | 5.19 |
| Adiponitrile, DMFA, Glycerine | " | " | 6.48 | 5.83 |
| Adiponitrile, DMFA, Propylene carbonate | " | " | 6.10 | 6.11 |
| Adiponitrile, Sulfolane, 1,4-Butanediol | " | " | 6.06 | 6.05 |
| Adiponitrile, Sulfolane, Ethylene glycol | " | " | 7.49 | 6.32 |
| Adiponitrile, Sulfolane, Ethylene carbonate | " | " | 6.24 | 6.70 |
| Adiponitrile, DMSO, Ethylene carbonate | " | " | 6.76 | 7.63 |
| Sulfolane, DMSO, Ethylene glycol | " | " | 8.34 | 9.88 |
| Sulfolane, DMSO, Triethylene glycol | " | " | 6.24 | 6.09 |
| Sulfolane, DMSO, Ethylene carbonate | " | " | 7.14 | 8.12 |
| Sulfolane, DMFA, Ethylene carbonate | " | " | 6.63 | 7.14 |
| Adiponitrile, DMSO, Sulfolane, Ethylene glycol | $(1/4)^4$ | $(2/7)^4$ | 6.30 | 6.54 |
| Adiponitrile, DMSO, Sulfolane, 1,4-Butanediol | " | " | 5.53 | 7.33 |
| Adiponitrile, DMSO, Sulfolane, 1,5-Pentanediol | " | " | 5.85 | 6.31 |
| Adiponitrile, DMSO, Sulfolane, Glycerine | " | " | 6.49 | 6.13 |

TABLE II

Extractive Distillation Agents Which Are Effective In Separating Isopropyl Ether From Methyl Ethyl Ketone

| Compound | Ratios | | Relative Volatilities | |
|---|---|---|---|---|
| Adiponitrile | 1 | 6/5 | 5.89 | 5.86 |
| Dimethylformamide (DMFA) | " | " | 4.24 | 4.72 |
| Propylene carbonate | " | " | 5.85 | 5.00 |
| Nitrobenzene | " | " | 2.93 | 3.02 |
| Sulfolane | " | " | 6.11 | 5.20 |
| Adiponitrile, Ethylene glycol | $(1/2)^2$ | $(3/5)^2$ | 5.86 | 6.13 |
| Adiponitrile, Propylene glycol | " | " | 5.96 | 5.92 |
| Adiponitrile, 1,6-Hexanediol | " | " | 4.82 | 5.30 |
| Adiponitrile, Tetraethylene glycol | " | " | 6.18 | 5.69 |
| Adiponitrile, Dipropylene glycol | " | " | 5.73 | 4.97 |
| Adiponitrile, Propylene carbonate | " | " | 5.81 | 6.05 |
| Adiponitrile, Sulfolane | " | " | 5.95 | 6.02 |

TABLE II-continued

Extractive Distillation Agents Which Are Effective In Separating Isopropyl Ether From Methyl Ethyl Ketone

| Compound | Ratios | | Relative Volatilities | |
|---|---|---|---|---|
| Adiponitrile, Hexylene glycol | " | " | 4.46 | 4.02 |
| DMFA, Ethylene glycol | " | " | 5.54 | 5.25 |
| DMFA, Propylene glycol | " | " | 4.51 | 4.74 |
| DMFA, 1,4-Butanediol | " | " | 4.09 | 5.63 |
| DMFA, 1,5-Pentanediol | " | " | 4.42 | 4.94 |
| DMFA, 1,6-Hexanediol | " | " | 4.32 | 4.39 |
| DMFA, Diethylene glycol | " | " | 4.78 | 4.27 |
| DMFA, Triethylene glycol | " | " | 4.68 | 4.75 |
| DMFA, Tetraethylene glycol | " | " | 5.04 | 4.66 |
| DMFA, Dipropylene glycol | " | " | 4.31 | 4.15 |
| DMFA, 3-Chloro-1,2-propanediol | " | " | 4.34 | 4.66 |
| DMFA, Polyethylene glycol 300 | " | " | 4.23 | 4.66 |
| DMFA, DMSO | " | " | 4.99 | 5.21 |
| Nitrobenzene, Ethylene glycol | " | " | 5.98 | 4.92 |
| Nitrobenzene, Propylene glycol | " | " | 3.91 | 3.54 |
| Nitrobenzene, 1,4-Butanediol | " | " | 4.18 | 4.05 |
| Nitrobenzene, Glycerine | " | " | 6.45 | 4.24 |
| Sulfolane, Propylene carbonate | " | " | 6.18 | 5.52 |
| Adiponitrile, DMSO, Propylene glycol | $(1/3)^3$ | $(2/5)^3$ | 6.26 | 5.25 |
| Adiponitrile, DMSO, Dipropylene glycol | " | " | 5.25 | 4.59 |
| Adiponitrile, DMSO, 1,6-Hexanediol | " | " | 4.65 | 4.96 |
| Adiponitrile, DMSO, Hexylene glycol | " | " | 4.99 | 5.43 |
| Adiponitrile, DMFA, Propylene glycol | " | " | 5.14 | 5.48 |
| Adiponitrile, DMFA, 1,4-Butanediol | " | " | 5.74 | 5.51 |
| Adiponitrile, DMFA, 1,5-Pentanediol | " | " | 5.39 | 5.59 |
| Adiponitrile, DMFA, 1,6-Hexanediol | " | " | 5.20 | 5.27 |
| Adiponitrile, DMFA, Hexylene glycol | " | " | 5.33 | 5.28 |
| Adiponitrile, DMFA, Ethylene carbonate | " | " | 5.78 | 6.14 |
| Adiponitrile, Sulfolane, Diethylene glycol | " | " | 4.78 | 5.26 |
| Adiponitrile, Nitrobenzene, Glycerine | " | " | 4.70 | 4.84 |
| DMSO, Nitrobenzene, Ethylene glycol | $(1/3)^3$ | $(2/5)^3$ | 4.48 | 4.64 |
| DMSO, Nitrobenzene, Propylene glycol | " | " | 4.78 | 4.63 |
| DMSO, Nitrobenzene, 1,4-Butanediol | " | " | 3.09 | 4.70 |
| DMSO, Methyl isoamyl ketone, Ethylene glycol | " | " | 4.38 | 3.69 |
| DMSO, Methyl isoamyl ketone, 1,4-Butanediol | " | " | 3.92 | 3.85 |
| DMSO, Methyl isoamyl ketone, Glycerine | " | " | 3.37 | 3.35 |
| DMFA, Nitrobenzene, Glycerine | " | " | 4.26 | 4.50 |
| DMFA, Ethylene glycol, Polyethylene glycol 300 | " | " | 4.73 | 4.80 |
| Sulfolane, DMSO, Propylene glycol | " | " | 5.25 | 5.16 |
| Sulfolane, DMSO, 1,4-Butanediol | " | " | 5.41 | 5.78 |
| Sulfolane, DMSO, 1,5-Pentanediol | " | " | 5.08 | 5.03 |
| Sulfolane, DMSO, 1,6-Hexanediol | " | " | 4.64 | 5.29 |
| Sulfolane, DMSO, Hexylene glycol | " | " | 4.19 | 4.62 |
| Sulfolane, DMSO, Diethylene glycol | " | " | 5.02 | 4.46 |
| Sulfolane, DMSO, Tetraethylene glycol | " | " | 4.67 | 4.96 |
| Sulfolane, DMSO, Dipropylene glycol | " | " | 4.61 | 4.61 |
| Sulfolane, DMSO, Polyethylene glycol 300 | " | " | 5.46 | 5.65 |
| Sulfolane, DMSO, Glycerine | " | " | 5.60 | 6.26 |
| Sulfolane, DMSO, 3-Chloro-1,2-propanediol | " | " | 5.28 | 5.31 |
| Sulfolane, DMSO, Ethylene glycol hexyl ether | " | " | 3.85 | 3.65 |
| Sulfolane, DMSO, Hexyl acetate | " | " | 3.58 | 3.44 |
| Sulfolane, DMSO, Propoxypropanol | " | " | 3.40 | 3.69 |
| Sulfolane, DMSO, Propylene carbonate | " | " | 5.39 | 4.62 |
| Adiponitrile, DMSO, Sulfolane, Propylene glycol | $(1/4)^4$ | $(2/7)^4$ | 5.31 | 5.55 |
| Adiponitrile, DMSO, Sulfolane, Neopentyl glycol | " | " | 4.54 | 4.78 |
| Adiponitrile, DMSO, Sulfolane, 1,6-Hexanediol | " | " | 5.22 | 5.53 |
| Adiponitrile, DMSO, Sulfolane, Hexylene glycol | " | " | 4.36 | 4.70 |
| Adiponitrile, DMSO, Sulfolane, Diethylene glycol | " | " | 5.56 | 5.58 |
| Adiponitrile, DMSO, Sulfolane, Triethylene glycol | " | " | 4.89 | 5.73 |
| Adiponitrile, DMSO, Sulfolane, Tetraethylene glycol | " | " | 5.52 | 5.87 |
| Adiponitrile, DMSO, Sulfolane, Dipropylene glycol | " | " | 4.80 | 5.28 |
| Adiponitrile, DMSO, Sulfolane, Polyethylene glycol | " | " | 5.95 | 5.85 |
| Adiponitrile, DMSO, Sulfolane, 3-Chloro-1,2-propanediol | " | " | 5.28 | 5.72 |

TABLE III

Extractive Distillation Agents Which Are Ineffective In Separating Isopropyl Ether From Methyl Ethyl Ketone

| Compounds | Ratios | | Relative Volatilities |
|---|---|---|---|
| Dimethylsulfoxide (DMSO) | 1 | | 2-phase |
| Ethylene glycol, DMSO | $(1/2)^2$ | $(3/5)^2$ | 2-phase |
| Ethylene glycol, Methyl isoamyl ketone | " | " | 2-phase |
| Glycerine, Methyl isoamyl ketone | " | " | 2-phase |
| 1,4-Butanediol, Methyl isoamyl ketone | " | " | 3.05  2.76 |
| Ethylene glycol, DMSO, DMFA | $(1/3)^3$ | $(2/5)^3$ | 2-phase |

TABLE IV

Data From Runs Made In Rectification Column

| Compounds | Overhead Temp., °C. | Stillpot Temp., °C. at Start | Stillpot Temp., °C. after 1.5 hrs. | Relative Volatility |
| --- | --- | --- | --- | --- |
| Blank | 63 | 78 | 76 | 2.55 |
| Adiponitrile | 64 | 78 | 115 | 10.08 |
| DMSO + Adiponitrile | 63.2 | 75.8 | 115.8 | 9.51 |
| DMSO(R) + Adiponitrile(R) | 62.6 | 75.6 | 109.2 | 9.46 |
| Sulfolane(R) + Adiponitrile(R) | 62.2 | 77.6 | 112.6 | 6.75 |
| DMSO(R) + Sulfolane(R) + Adiponitrile(R) | 62.8 | 77.8 | 112.0 | 7.24 |
| DMSO(R) + Glycerine + Adiponitrile(R) | 61.6 | 78.8 | 104 | 5.09 |

The ratios shown in Tables I, II and III are the parts by weight of extractive agent used per part of isopropyl ether—methyl ethyl ketone mixture and the two relative volatilities correspond to the two different ratios. For example in Table I, one part of ethylene carbonate with one part of isopropyl ether—methyl ethyl ketone mixture gives a relative volatility of 8.91, 6/5 parts of ethylene carbonate gives 8.35. One half part of adiponitrile mixed with one half part of 1,4-butanediol with one part of the isopropyl ether—methyl ethyl ketone mixture gives a relative volatility of 6.59, 3/5 parts of adiponitrile plus 3/5 parts of 1,4-butanediol gives 6.31. One third parts of adiponitrile plus ⅓ parts of DMSO plus ⅓ parts of ethylene glycol mixed with one part of isopropyl ether—methyl ethyl ketone mixture gives a relative volatility of 6.68, with 2/5 parts, these three give 7.02.

Table III lists a few combinations of some of the same compounds presented in Tables I and II which failed to give relative volatilities as high as 3.0. This is principally due to the formation of two phase azeotropes which have the effect of bringing the extractive agent as part of the overhead.

Several of the compounds and mixtures listed in Tables I and II and whose relative volatility had been determined in the vapor-liquid equilibrium still, were then evaluated in a glass perforated plate rectification column possessing 4.5 theoretical plates. The results are listed in Table IV. The isopropyl ether—methyl ethyl ketone mixture studied contained 5% isopropyl ether, 95% methyl ethyl ketone. The isopropyl ether—methyl ethyl ketone azeotrope contains 87.6 wt.% isopropyl ether, 12.4 wt.% methyl ethyl ketone. What is remarkable is that pure isopropyl ether comes off as overhead product. In every case the feed or bottoms composition contained less than 87.6% isopropyl ether and in every case the overhead is richer than 87.6% isopropyl ether. Without extractive distillation agents, the overhead would be the azeotrope, 87.6% isopropyl ether. This proves that the extractive agent is negating the azeotrope and makes the rectification proceed as if the azeotrope no longer existed and brings the more volatile component, isopropyl ether, out as overhead.

The data in Table IV was obtained in the following manner. The charge designated "blank" was 5% isopropyl ether, 95% methyl ethyl ketone and after 1.5 hours operation in the 4.5 theoretical plate column, the relative volatility of the separation between the isopropyl ether—methyl ethyl ketone azeotrope and methyl ethyl ketone was 2.55. The remaining data is for the extractive distillation agents designated. Here we have negated the azeotrope and brought out the pure isopropyl ether as overhead. The temperature of the overhead approaches 63° C., the boiling point of pure isopropyl ether at 630 mm. Hg. and the methyl ethyl ketone goes to the stillpot with the extractive distillation agent. The designation "R" by the extractive distillation agent means that the same material was recovered and re-used to show its stability in repeated operation. When the methyl ethyl ketone—extractive distillation agent mixture taken from the stillpot is redistilled, methyl ethyl ketone comes off overhead in the usual way at its normal boiling point, 79.6° C.

THE USEFULNESS OF THE INVENTION

The usefulness or utility of this invention can be demonstrated by referring to the data presented in Table I, II, III and IV. All of the successful extractive distillation agents show that isopropyl ether can be removed from its binary minimum azeotrope with methyl ethyl ketone by means of distillation in a rectification column and that the ease of separation as measured by relative volatility is considerable. Without the extractive distillation agents, no improvement above the azeotrope composition will occur in the rectification column. The data also show that the most attractive agents will operate at a boilup rate low enough to make this a useful and efficient method of recovering high purity isopropyl ether from any mixture with methyl ethyl ketone including the minimum azeotrope. The stability of the compounds used and the boiling point difference is such that complete recovery and recycle is obtainable by a simple distillation and the amount required for make-up is small.

WORKING EXAMPLES

Example 1

The isopropyl ether—methyl ethyl ketone azeotrope is 88% isopropyl ether, 12% methyl ethyl ketone. Twenty-five grams of isopropyl ether, 25 grams of methyl ethyl ketone and 50 grams of ethylene carbonate were charged to an Othmer type glass vapor-liquid equilibrium still and refluxed for 11 hours. Analysis of the vapor and liquid by gas chromatography gave vapor 79.2% isopropyl ether, 20.8% methyl ethyl ketone; liquid of 30% isopropyl ether, 70% methyl ethyl ketone. This indicates a relative volatility of 8.91. Ten grams of ethylene carbonate were added and refluxing continued for another nine hours. Analysis indicated a vapor composition of 77.9% isopropyl ether, 22.1% methyl ethyl ketone, a liquid composition of 29.2% isopropyl ether, 70.8% methyl ethyl ketone which is a relative volatility of 8.35.

Example 2

Twenty-five grams of isopropyl ether, 25 grams of methyl ethyl ketone, 25 grams of adiponitrile and 25 grams of 1,4-butanediol were charged to the vapor-liquid equilibrium still and refluxed for 16 hours. Analysis indicated a vapor composition of 77.3% isopropyl ether, 22.7% methyl ethyl ketone, a liquid composition of 34.1% isopropyl ether, 65.9% methyl ethyl ketone which is a relative volatility of 6.59. Five grams of adiponitrile and five grams of 1,4-butanediol were added and refluxing continued for another 11 hours. Analysis indicated a vapor composition of 73.6% isopropyl ether, 26.4% methyl ethyl ketone, a liquid composition of 30.6% isopropyl ether, 69.4% methyl ethyl ketone which is a relative volatility of 6.31.

Example 3

Twenty-five grams of isopropyl ethyl, 25 grams of methyl ethyl ketone, 17 grams of adiponitrile, 17 grams of DMSO and 17 grams of ethylene glycol were charged to the vapor-liquid equilibrium still and refluxed for 16 hours. Analysis indicated a vapor composition of 78.8% isopropyl ether, 21.2% methyl ethyl ketone, a liquid composition of 35.8% isopropyl ether, 64.2% methyl ethyl ketone which is a relative volatility of 6.68. Three grams each of adiponitrile, DMSO and ethylene glycol were added and refluxing continued for another 11 hours. Analysis indicated a vapor composition of 77.2% isopropyl ether, 22.8% methyl ethyl ketone, a liquid composition of 32.5% isopropyl ether, 67.5% methyl ethyl ketone which is a relative volatility of 7.02.

Example 4

A glass perforated plate rectification column was calibrated with ethylbenzene and p-xylene which possesses a relative volatility of 1.06 and found to have 4.5 theoretical plates. A solution of 25 grams of isopropyl ether and 475 grams of methyl ethyl ketone was placed in the stillpot and heated. When refluxing began, an extractive agent comprising pure adiponitrile was pumped into the column at a rate of 20 ml/min. The temperature of the extractive agent as it entered the column was 58±2° C. After establishing the feed rate of the extractive agent, the heat input to the isopropyl ether and methyl ethyl ketone in the stillpot was adjusted to give a total reflux rate of 10–16 ml/min. After one hour of operation, the overhead and bottoms samples of approximately two ml. were collected and analysed using gas chromatography. The overhead analysis was 99.8% isopropyl ether, 0.2% methyl ethyl ketone. The bottoms analysis was 1.5% isopropyl ether, 98.5% methyl ethyl ketone. Using these compositions in the Fenske equation, with the number of theoretical plates in the column being 4.5, gave an average relative volatility of 10.08 for each theoretical plate.

Example 5

A solution of 25 grams of isopropyl ether and 475 grams of methyl ethyl ketone was placed in the stillpot of the same column used in example 4 and heat applied. When the refluxing began, an extractive agent of 50% DMSO and 50% adiponitrile was fed into the top of the column at a feed rate of 20 ml/min. and a temperature of 58° C. After establishing the feed rate of the extractive agent, the heat input to the isopropyl ether and methyl ethyl ketone in the stillpot was adjusted to give a total reflux rate of 10–16 ml/min. Having established the reflux ratio, the column was allowed to operate for one hour. After one hour of steady operation, overhead and bottoms samples of approximately two ml. were collected and analysed using gas chromatography. The overhead analysis was 99.7% isopropyl ether, 0.3% methyl ethyl ketone, the bottoms analysis was 1.3% isopropyl ether, 98.7% methyl ethyl ketone. Using these compositions in the Fenske equation with the number of theoretical plates of the column being 4.5, gave an average relative volatility 9.51 for each theoretical plate.

Example 6

A solution of 25 grams of isopropyl ether and 475 grams of methyl ethyl ketone was placed in the stillpot of the same column used in example 4 and heat applied. When refluxing began, an extractive agent comprising 33% DMSO, 33% sulfolane and 33% adiponitrile was fed into the top of the column at a feed rate of 20 ml/min and a temperature of 58° C. After establishing the feed rate of the extractive agent, the heat input to the isopropyl ether and methyl ethyl ketone in the stillpot was adjusted to give a total reflux rate of 10–16 ml/min. Having established the reflux rate, the column was allowed to operate for one hour. After one hour of steady operation, overhead and bottoms samples of approximately two ml. were collected and analysed using gas chromatography. The overhead analysis was 98.8% isopropyl ether, 1.2% methyl ethyl ketone and the bottoms analysis was 1.1% isopropyl ether, 98.9% methyl ethyl ketone. Using these compositions in the Fenske equation and with the number of theoretical plates in the column being 4.5, gave an average relative volatility of 7.24 for each theoretical plate.

Example 7

A solution of 25 grams of isopropyl ether and 475 grams of methyl ethyl ketone was placed in the stillpot of the same column used in example 4 and heat applied. When refluxing began, an an extractive agent comprising pure adiponitrile was fed into the top of the column at a temperature of 58° C. The heat input to the stillpot was adjusted to give a total reflux rate of 10–16 ml/min. and 1.5 hours allowed for the column to reach equilibrium. For the first run the feed rate of the adiponitrile was 20 ml/min., for the second run it was dropped to 10 ml/min., for the third run it was again dropped to 5 ml/min. and for the fourth run it was increased back to the original 20 ml/min. rate. For each run after the first, the adiponitrile was reclaimed and reused. The following data was obtained:

| Run No. | Feed Rate, ml/min. | Wt. % Isopropyl ether Overhead | Bottoms | Relative Volatility |
|---|---|---|---|---|
| 1 | 20 | 99.7 | 1.3 | 9.51 |
| 2 | 10 | 98.0 | 1.1 | 6.45 |
| 3 | 5 | 94.9 | 1.4 | 4.93 |
| 4 | 20 | 99.7 | 1.3 | 9.51 |

As the rate of feed of the extractive agent is reduced, the relative volatility declines from 9.51 at 20 ml/min. to 4.93 at 5 ml/min. When the feed rate is restored to 20 ml/min., the relative volatility goes back to 9.51. This shows the importance of using the proper feed rate in extractive distillation.

The nature of the present invention having been described, what we wish to claim as new and useful and secure by Letters Patent is:

1. A method for recovering isopropyl ether from a mixture of isopropyl ether and methyl ethyl ketone which comprises distilling a mixture of isopropyl ether and methyl ethyl ketone in a rectification column in the presence of an effective amount of an extractive agent, recovering essentially pure isopropyl ether as overhead and obtaining the extractive agent and methyl ethyl ketone from the stillpot or reboiler, the extractive agent comprises at least adiponitrile.

2. The method of claim 1 in which the extractive agent comprises a mixture of adiponitrile and at least one material from the group consisting of: ethylene glycol, propylene glycol, 1,4-butanediol, 1,5-pentanediol, 1,6-hexanediol, diethylene glycol, triethylene glycol, tetraethylene glycol, hexylene glycol, glycerine, dipropylene glycol, ethylene carbonate, propylene carbonate, nitrobenzene and dimethylformamide.

3. A method for recovering isopropyl ether from a mixture of isopropyl ether and methyl ethyl ketone which comprises distilling a mixture of isopropyl ether and methyl ethyl ketone in a rectification column in the presence of an effective amount of an extractive agent, recovering essentially pure isopropyl ether as overhead and obtaining the extractive agent and methyl ethyl ketone from the stillpot or reboiler, the extractive agent comprises at least dimethylformamide.

4. The method of claim 3 in which the extractive agent comprises a mixture of dimethylformamide and at least one material from the group consisting of: ethylene carbonate, ethylene glycol, propylene glycol, 1,4-butanediol, 1,5-pentanediol, 1,6-hexanediol, diethylene glycol, triethylene glycol, tetraethylene glycol, dipropylene glycol, 3-chloro-1,2-propanediol, polyethylene glycol, glycerine and nitrobenzene.

5. A method for recovering isopropyl ether from a mixture of isopropyl ether and methyl ethyl ketone which comprises distilling a mixture of isopropyl ether and methyl ethyl ketone in a rectification column in the presence of an effective amount of an extractive agent, recovering essentially pure isopropyl ether as overhead and obtaining the extractive agent and methyl ethyl ketone from the stillpot or reboiler, the extractive agent comprises at least nitrobenzene.

6. The method of claim 5 in which the extractive agent comprises a mixture of nitrobenzene and at least one material from the group consisting of: ethylene glycol, propylene glycol, 1,4-butanediol and glycerine.

7. A method for recovering isopropyl ether from a mixture of isopropyl ether and methyl ethyl ketone which comprises distilling a mixture of isopropyl ether and methyl ethyl ketone in a rectification column in the presence of an effective amount of an extractive agent, recovering essentially pure isopropyl ether as overhead and obtaining the extractive agent and methyl ethyl ketone from the stillpot or reboiler, the extractive agent comprises at least ethylene carbonate.

8. A method for recovering isopropyl ether from a mixture of isopropyl ether and methyl ethyl ketone which comprises distilling a mixture of isopropyl ether and methyl ethyl ketone in a rectification column in the presence of an effective amount of an extractive agent, recovering essentially pure isopropyl ether as overhead and obtaining the extractive agent and methyl ethyl ketone from the stillpot or reboiler, the extractive agent comprises at least propylene carbonate.

* * * * *